United States Patent
Wilhelmsen

(12) 
(10) Patent No.: US 6,248,760 B1
(45) Date of Patent: Jun. 19, 2001

(54) TABLET GIVING RAPID RELEASE OF NICOTINE FOR TRANSMUCOSAL ADMINISTRATION

(76) Inventor: Paul C Wilhelmsen, 281 Livoina Hgts, Alamo, CA (US) 94507

( * ) Notice: Subject to any disclaimer, the term of this patent is extended or adjusted under 35 U.S.C. 154(b) by 0 days.

(21) Appl. No.: 09/292,045

(22) Filed: Apr. 14, 1999

(51) Int. Cl.$^7$ .......................... A61K 31/465; A61K 9/00; A61K 33/06; A61K 47/00

(52) U.S. Cl. .......................... 514/343; 424/434; 424/435; 424/464; 424/466; 424/468; 424/471; 424/472; 424/474; 424/682; 424/686; 424/687; 424/688; 424/692; 514/769; 514/810; 514/813; 514/819; 514/960

(58) Field of Search .................................. 424/435, 464, 424/468, 472, 400, 434, 471, 474, 682, 686, 687, 688, 692, 457, 458, 463, 466, 443, 445, 446, 447, 448, 449; 514/343, 769, 810, 813, 819, 960, 962

(56) References Cited

U.S. PATENT DOCUMENTS

| | | | |
|---|---|---|---|
| 865,026 | * 9/1907 | Ellis | 131/352 |
| 3,845,217 | * 10/1974 | Ferno et al. | 426/3 |
| 3,877,468 | * 4/1975 | Lichtneckert et al. | 131/359 |
| 3,901,248 | * 8/1975 | Lichtneckert et al. | 131/359 |
| 4,284,089 | * 8/1981 | Ray | 131/270 |
| 4,579,858 | * 4/1986 | Ferno et al. | 514/343 |
| 4,655,231 | * 4/1987 | Ray et al. | 131/359 |
| 4,671,953 | * 6/1987 | Stanley et al. | 424/440 |
| 4,764,378 | * 8/1988 | Keith et al. | 424/435 |
| 4,806,356 | * 2/1989 | Shaw | 424/440 |
| 4,839,174 | * 6/1989 | Baker et al. | 424/447 |
| 4,907,605 | * 3/1990 | Ray et al. | 131/270 |
| 4,943,435 | * 7/1990 | Baker et al. | 424/448 |
| 4,953,572 | * 9/1990 | Rose et al. | 131/270 |
| 5,016,652 | * 5/1991 | Rose et al. | 131/270 |
| 5,035,252 | * 7/1991 | Mondre | 132/321 |
| 5,048,544 | * 9/1991 | Macarelli et al. | 131/270 |
| 5,120,546 | * 6/1992 | Hansen et al. | 424/449 |
| 5,135,753 | * 8/1992 | Baker et al. | 424/435 |
| 5,147,654 | * 9/1992 | Place et al. | 424/473 |
| 5,167,964 | * 12/1992 | Muhammad et al. | 424/482 |
| 5,284,163 | * 2/1994 | Knudsen et al. | 131/270 |
| 5,288,497 | * 2/1994 | Stanley et al. | 424/440 |
| 5,334,390 | * 8/1994 | Solomon et al. | 424/439 |
| 5,488,962 | * 2/1996 | Perfetti | 131/270 |
| 5,525,351 | * 6/1996 | Dam | 424/440 |
| 5,549,906 | * 8/1996 | Santus | 424/440 |
| 5,593,684 | * 1/1997 | Baker et al. | 424/435 |
| 5,633,008 | * 5/1997 | Osborne et al. | 424/448 |
| 5,645,088 | * 7/1997 | Olovson | 131/270 |
| 5,666,979 | * 9/1997 | Chase | 131/270 |
| 5,733,574 | * 3/1998 | Dam | 424/464 |
| 5,785,989 | * 7/1998 | Stanley et al. | 424/440 |
| 5,810,018 | * 9/1998 | Monte | 131/270 |
| 5,834,011 | * 11/1998 | Rose et al. | 424/449 |
| 5,865,186 | * 2/1999 | Volsey | 131/194 |
| 5,869,098 | * 2/1999 | Misra et al. | 424/484 |
| 5,875,786 | * 3/1999 | Chase | 131/270 |
| 6,120,802 | * 9/2000 | Breitenbach et al. | 424/464 |

FOREIGN PATENT DOCUMENTS

97/42941 * 11/1997 (WO).

OTHER PUBLICATIONS

Jarvik et al., 'Inhibition of cigarette smoking by orally administered nicotine', Clinical Pharmacology and Therapeutics (1970), vol. 11, No. 4, pp. 574–576.*

Russell et al., 'Nasal nicotine solution:a potential aid to giving up smoking?', British Medical Journal (1983), vol. 286, pp. 683, 686.*

Henningfield et al., 'Higher levels of nicotine in arterial than in venous blood after cigarette smoking', Drug and Alcohol Dependence (1993), vol. 33, pp. 23–29.*

Feyerabend et al., 'Nicotine pharmacokinetics and its application to intake from smoking',Br. J. Clin. Pharmac. (1985), vol. 19, pp. 239–247.*

Warburton et al., 'Facilitation of learning and state dependency with nicotine', Psychopharmacology (1986), vol. 89, pp. 55–59.*

Frith, 'The effects of nicotine on tapping:I', Life Sciences (1967), vol. 6, pp. 313–319.*

Frith, 'The effects of nicotine on tapping:II', Life Sciences (1967), vol. 6, pp. 321–326.*

Gehlbach et al., 'Green–tobacco sickness',JAMA (1974), vol. 229, No. 14, pp. 1880–1883.*

Sahakian et al.'The effects of nicotine on attention, information processing, and short–term memory in patients with dementia of alzheimer type',British Journal of Psychiatry (1989), vol. 154, pp. 797–800.*

Pomerleau et al.,'Controlled dosing of nicotine via an Intransal Nicotine Aerosol Delivery Device (INADD)', Psychopharmacology (1992), vol. 108, pp. 519–526.*

Soria et al.,'Subjective and cardiovascular effects of intravenous nicotine smokers and non–smokers', Psychopharmacology (1996), vol. 128, pp. 221–226.*

Travell,'Absorption of nicotine from various sites',Annals New York Academy of Sciences (1960), vol. 90, pp. 13–30.*

Larson,'Absorption of nicotine under various conditions of tobacco use',Annals New York Academy of Sciences (1960), vol. 90, pp. 31–35.*

Lucchesi et al.,'The role of nicotine as a determinant of cigarette smoking frequency in man with observations of certain cardiovascular effects associated with the tobacco alkaloid',Clinical Pharmacology and Therapeutics (1967), vol. 8, No. 6,pp. 789–796.*

(List continued on next page.)

Primary Examiner—John Pak
Assistant Examiner—Frank Choi

(57) ABSTRACT

A tablet for the transmucosal administration of nicotine. The nicotine is in one or more layers upon a non-nicotine containing matrix. The nicotine layers rapidly dissolve in the mouth. The nicotine is then rapidly absorbed by the intraoral mucosal surfaces. The short, rapid pulse of nicotine is similar to that given by cigarette smoking. The nicotine may be provided in a plurality of layers separated by one or more layers that are essentially free of nicotine to support the nicotine layers.

15 Claims, 1 Drawing Sheet

OTHER PUBLICATIONS

Johnston, 'Tobacco smoking and nicotine', The Lancet (1942), vol. CCXLIII, p. 742.*

Benowitz et al.,'Intravenous nicotine replacement suppresses nicotine intake from cigarette smoking', The Journal of Pharmacology and Experimental Therapeutics (1990), vol. 254, No. 3, pp. 1000–1005.*

Benowitz,'Nicotine pharmacology and addiction', Nicotine Safety and Toxicity (1998), pp. 3–16.*

Stitzer et al.,'Abuse liability of nicotine', Nicotine Safety and Toxicity (1998), pp. 119–131.*

Russell,'Nicotine replacement: The role of blood nicotine levels, their rate of change, and nicotine tolerance', Nicotine Replacement: A Critical Evaluation (1988), pp. 63–94.*

Wesnes et al.,'The separate and combined effects of scopolamine and nicotine on human information processing', Psychopharmacology (1984), vol. 84, pp. 5–11.*

Beckett et al.,'A possible relation between pKa1 and lipid solubility and the amounts excreted in urine of some tobacco alkaloids given to man', J. Pharm. Pharmac. (1972), vol. 24, pp. 115–120.*

* cited by examiner

TABLET GIVING RAPID RELEASE OF NICOTINE FOR TRANSMUCOSAL ADMINISTRATION

BACKGROUND

1. Field of Invention

The present invention relates to a tablet for transmucosal administration of a medicament. Specifically, it relates to a tablet that will give a rapid release of nicotine.

2. Description of Prior Art

Nicotine is the most widely distributed of the plant alkaloids. It occurs in two separate phyla of the plant kingdom, Pteridophytes and Spermatophytes. Despite its wide distribution, for practical purposes, nicotine is obtained from the *tabacum* and *rustica* species of the Nicotina genus. However, it is interesting that Australian Aboriginal people chewed "pituri", a nicotine preparation made from *Duboisia hopoodi*.

Nicotine can be isolated as an oily, volatile base with a sharp burning taste. Nicotine will form acid salts with most acids. Nicotine can be introduced into the body in many ways. The most popular way is by smoking cigarettes. When a cigarette is smoked, the partial oxidation of the tobacco causes the vaporizing of some of the nicotine. The nicotine vapor as well as nicotine adsorbed on partial oxidation products of the cigarette is quickly absorbed through the lungs. A dozen beats of the heart can carry nicotine from the lungs to the brain in less than 20 seconds.

Smoking cigarettes introduces many undesirable materials into the person smoking, as well as into the environment. Because of this, most smokers would like to quit smoking. However, a craving for nicotine, irritability, restlessness, difficulty in concentrating, headaches, an increase in weight, and anxiety often follow cessation of smoking. Supplying nicotine in an alternative way has been helpful in some cases of those wishing to quit smoking. Several alternative ways of delivering nicotine have been proposed.

Pomerleau (Psychopharmacology 1992, 108, 519–526) listed some of the criteria that should be met for an alternative nicotine dosing method to be considered satisfactory: 1) the method should be safe and easy to use; 2) specified doses should be accurately and reproducibly delivered; and 3) the pharmacokinetics should resemble those of cigarette smoking. The following is a review of the major alternative nicotine dosing methods and their drawbacks, i.e., how they fail or meet these criteria.

Frith (Life Sciences, 1967, 6, 321–326) described experiments where tablets containing 0.1 mg of nicotine were administered orally. The subjects were instructed to chew the tablets until the tablets were dissolved. These tablets had the nicotine distributed uniformly throughout the tablets. The pharmacokinetics did not resemble those of cigarette smoking.

Lennox M. Johnston and M. D. Glasg in the Dec. 19, 1942 edition of Lancet, p.742, described intravenous injection of nicotine. They reported that after several injections, an injection was preferred to a cigarette. Intravenous injection has continued to be used in scientific experimentation. See for example Lucchesi et al. (Clin. Pharm. Ther., 1967, 8, 789–96), Soria et al. (Psychopharmacology 1996, 128, 1000–1005), Benowitz et al. (J. of Pharmacol. Exp. Ther. 1990, 254, 1000–1005), and Rosenberg et al. (Clin. Pharmacol. Exp. Ther. 1980, 28, 516–22). However, intravenous injection is obviously not a suitable replacement for smoking in most situations.

Jarvik et al. (Clin. Pharm. Ther. 1970,11, 574–576) described experiments where 10 mg tablets of nicotine tartrate were swallowed at two hour intervals by several subjects. The idea was that although the ionic form of nicotine would not be absorbed in the stomach, it would be absorbed in the intestine. However, most of the nicotine absorbed in the intestine is metabolized by the liver before it reaches the nervous system. The large amounts of nicotine in these experiments, as compared with about 1 mg available in a cigarette, had only a small effect. (Actually the abstract of this paper states that 10 mg of nicotine tartrate per kilogram was administered, but this is an obvious error.) The pharmacokinetics of swallowed nicotine did not resemble smoking.

Wesnes and Warburton (Psychopharmacology, 1984, 82, 147–150) described experiments where nicotine was added to dextrose tablets. They also (Psychopharmacology, 1986, 89, 55–59) used nicotine absorbed in magnesium hydroxide pills. In their experiments they covered the taste of nicotine with hot pepper sauce. The sauce is acidic. Travel (Ann. New York Ac. Sc., 1960, 80, 13–32) had found that nicotine is more readily absorbed in its base form rather than as its acid salts. Beckett et al. (J. of Pharmacy and Pharmacology, 1971, 24, 115–120) had found that solutions of nicotine were more rapidly absorbed in the buccal cavity if they had an alkaline pH. Under the conditions of the experiments by Wesnes and Warburton, the alkaline reaction of the basic magnesium hydroxide would be useful. In the experiments of Wesnes and Warbuton a dilute nicotine solution was allowed to soak into the dextrose or magnesium hydroxide pills. The subjects were requested to hold the pills in their mouths for 5 minutes before swallowing. The described pills did not give a rapid release of nicotine.

Shaw (U.S. Pat. No. 4,806,356, 1989) described a lozenge made by compression molding with nicotine distributed uniformly throughout. Shaw's lozenges will slowly release nicotine. Santus (U.S. Pat. No. 5,549,906, 1996) described nicotine-containing lozenges where the nicotine is uniformly distributed through a nonnutritive sweetener and an absorbent excipient. Santus discussed how the administration of nicotine is obtained by allowing the lozenge to completely dissolve in the mouth. Several nicotine lozenges have been commercialized and are available as over-the-counter products in the U.K. These contain 0.5 mg nicotine distributed uniformly throughout the lozenges. The pharmacokinetics of these methods of dosing is not like smoking.

Sahakian et al. (Brit. J. Psychiatry, 1989,154, 797–800) described using a subcutaneous injection of nicotine. While of possible use in scientific studies, this does not fill the need for the usual smoker. Under some conditions, such an injection can cause severe muscular irritation.

The absorption of drugs such as nitroglycerin and scopolamine through the skin is a common occurrence. The absorption of nicotine through the skin has also long been known. Workers coming into physical contact with dew on tobacco leaves can develop what is called "green tobacco sickness". See for example Gehlbach et al. (J.A.M.A., 1974, 229, 1880–1883). The transdermal administration of nicotine has been the subject of many patents. For example, Baker et al. U.S. Pat. No. 4,839,174, 1989, U.S. Pat. No. 4,943,435, 1990, and U.S. Pat. No. 5,135,753, 1992. The commercial products based on these patents have turned out to be quite expensive. More importantly, the patches give a rather constant level of nicotine in the blood. Transdermal nicotine patches have another disadvantage in that it is difficult to administer nicotine at the rate required by different subjects. Benowitz et al. (J. Pharmacol. Exp. Ther., 1982, 21, 368–373) and Feyerabend et al. (Brit. J. Clin. Pharmacol. 1985, 19, 239–249) have found that there are up to four-fold variations in the rate nicotine is eliminated by smokers. It is also advantageous for users to be able to vary dosage to cope with times of intense craving.

Nicotine chewing gum is another way of administering nicotine. Ellis et al. (U.S. Pat. No. 865,026, 1907) provides an early example. More recent examples are Ferno et al. (U.S. Pat. No. 3,845,217, 1974) and Lichtneckert et al. (U.S. Pat. No. 3,877,468, 1975 and U.S. Pat. No. 3,901,248, 1975). Products of these patents are now being marketed on an international scale. These products combine a nicotine-containing cation exchange resin complex in a gum base. However, chewing gum is not socially acceptable in some circumstances. Some users of nicotine gum have complained about the effort required to chew it. Many users complain about the taste. The pharmacokinetics are different than smoking.

Much has been learned in recent years. Russell (Nicotine Replacement: A Critical Evaluation: Pomerleau, O. F. and Pomerleau, C. S., eds.; Alan R. Liss, Inc.: New York 1988, 63–94) observed that cigarette smoking provides an initial sharp rise in blood nicotine level which is missing in transdermal nicotine and in nicotine gum. Henningfield et al. (Drug Alcohol Dependence, 1993, 33, 23–39) showed that the arteriovenous differences during cigarette smoking are substantial, with arterial levels exceeding venous levels six- to ten-fold. Benowitz (Nicotine Safety and Toxicity, Benowitz, Neal L., ed.; Oxford: New York 1998, 3–16) observed that there is an intense pharmacological response due to the high levels of nicotine entering the brain and the effects occurring rapidly before the development of tolerance. The nicotine level in the brain declines between cigarettes as the nicotine is distributed to other body tissues. This decline in nicotine level provides an opportunity for resensitization of receptors, allowing some positive reinforcement despite the development of tolerance.

These conclusions have been verified by Stitzer and DeWit (Nicotine Safety and Toxicity, Benowitz, Neal L., ed.; Oxford: New York 1998, 119–131) where they measured the acceptance by cigarette smokers of an intravenous injection, a nasal spray, a vapor inhaler, nicotine gum, and a nicotine patch. A rating scale was used where the subjects gave 0 for liking "not at all" and 4 for liking "awful lot". Both the 2 and 4 mg. nicotine gums were given negative ratings. The nasal spray, the vapor inhaler and the nicotine patch all were given ratings of about 0. The average rating by the subjects for an injection of 1.5 mg of nicotine was 0.8 and for 3 mg the rating was 2.6. The average ratings for 1.4 mg cigarettes was 1.5 and for 2.9 mg cigarettes was 1.8. The high rating of the intravenous injection shows that a rapid increase in venous levels can give brain nicotine levels that give satisfaction to the smoker. However, nicotine administration by means that did not give a rapid increase in nicotine level was not found acceptable.

There have been several proposals to overcome the failure of transdermal patches and nicotine gum to deliver the sharp peak in blood nicotine level that is necessary to satisfy many smokers. For example, Rose et al. (U.S. Pat. No. 5,834,011, 1998) suggested using a nasal spray to give a rapid administration of nicotine. Rose suggested further that the aerosol be combined with transdermal patches. The aerosol delivery system is inconvenient and unpleasant for the user, as well as being expensive.

Baker et al. (U.S. Pat. No. 5,135,753, 1992) suggested combining transdermal patches with buccal administration of nicotine. The suggested tablets have their nicotine distributed uniformly and will not give the rapid release of nicotine that is lacking in the transdermal patches.

Perfetti (U.S. Pat. No. 5,488,962, 1996) has addressed some of the problems with the present nicotine gum. Perfetti proposed elimination of the cation-exchange resin and to use lower levels of nicotine in the gum. The improved gum described by Perfetti is still not convenient for the user. The improved gum will still not give the sharp nicotine peak that is desired.

Russell et al. (Brit. Med. J, 1983, 286, 683–684) described a nasal solution that could deliver nicotine via the nose. A two-percent solution of nicotine was combined with a thickening agent. Each dose was contained in a plastic container that could be opened and squeezed to administer the nicotine. These doses have the disadvantage of being expensive to manufacture and inconvenient to use. Ferno et al. was granted U.S. Pat. No. 4,579,588, 1986 for a similar idea.

Ray et al. (U.S. Pat. No. 4,655,231, 1987) described a synthetic snuff, which consists of a powdered salt of nicotine diluted with powdered organic sugars. Snuff is inconvenient for the user and is not socially acceptable.

Pomerleau et al. (Psychopharmacology, 1992, 108, 518–526) described an intranasal aerosol delivering system. This is an excellent method of delivering nicotine in a laboratory. It is capable of giving the short, intense pulses of nicotine that are desired. However, it is inconvenient for the user and not practical in most applications outside the laboratory.

Misra et al. (U.S. Pat. No. 5,869,098, 1999) described a device for making comestible units. These units might contain nicotine. The nicotine would be distributed uniformly through the units. The process for making these units is complicated and expensive.

Ray (U.S. Pat. No. 4,284,089, 1981) described the use of a device to vaporize nicotine. Unfortunately, nicotine vapor has a bad taste and the described device does not provide sufficient nicotine to satisfy cigarette smokers. This device is not convenient for the user and is expensive.

Volsey, II (U.S. Pat. No. 5,865,186, 1999) described a heated device that might overcome the problem that the Ray's device had in terms of the quantity of nicotine available. This device is not convenient for the user and is complicated.

Keith and Snipes (U.S. Pat. No. 4,764,378, 1988) described a buccal dosage form for transmucosal administration of nicotine. Their device attaches itself within the mouth and delivers the drug over several minutes. This device has the same disadvantages as nicotine gum.

Knudsen and Rasmussen (U.S. Pat. No. 5,284,163, 1994) described a device for administering a powdered or granular material containing nicotine into the oral cavity. The nicotine containing material is chewed together with gum. Their device has the same disadvantages as the nicotine gum.

Ray and Ellis patented an oral nicotine dispenser. Their U.S. Pat. No. 4,907,605, 1990, is specifically designed to slowly release nicotine. The nicotine is sorbed into polymeric materials. Ray and Ellis described the release of thirty percent of the nicotine per hour.

Rose et al. (U.S. Pat. No. 4,953,572, 1990) described the use of an aerosol to deliver nicotine to the oral cavity of an individual. As stated, this is an effective way of supplying nicotine to be absorbed rapidly. However, it is complicated, unpleasant for the user, and expensive.

Mondre received U.S. Pat. No. 5,035,252 in 1990. The Mondre patent covers using a dental floss containing nicotine. While it is quite likely that nicotine will be absorbed from nicotine containing dental floss, it is unlikely that cigarette smokers would be willing to floss as often as they would smoke a cigarette.

Mascarelli patented a lollypop that contained nicotine. His U.S. Pat. No. 5,048,544, 1991, is based on the assumption that smokers would accept lollypops as socially acceptable. To actually function, the lollypop would need to be placed in the mouth for a short time. Then must the wet, sticky lollypop be removed from the mouth for minutes, or even hours. In the event a lower concentration of nicotine is employed, the lollypop can left in the mouth but would not give the initial high dose of nicotine that has been shown to be required.

Place et al. (U.S. Pat. No. 5,147,654, 1992) described a complicated osmotic device for delivering nicotine. The device basically delivers nicotine at a constant rate over an extended time period.

Chase (U.S. Pat. No. 5,666,979, 1997, U.S. Pat. No. 5,875,786) described a cigar like carrier for nicotine. When the end of this device is chewed, the nicotine containing material is slowly released in the mouth. The nicotine is absorbed through the buccal mucous. This is complicated to manufacture and inconvenient to use.

Monte (U.S. Pat. No. 5,810,018, 1998) described a complicated procedure involving sprays containing nicotine, a sequestering agent and one or more stimulants. This procedure is difficult to implement and is expensive.

Olovson (U.S. Pat. No. 5,645,088, 1997) described a device adapted to be held between the frontal teeth and the inner surface of the lips. The peripheral part of the holder is made of a saliva-dissolvable material, which in some cases contains nicotine. This is a complicated way of getting nicotine to be absorbed in the mouth.

Dam (U.S. Pat. No. 5,525,351,1996 and U.S. Pat. No. 5,733,574, 1998) described a nicotine-containing gel. These units are designed to have a disintegration time of 5–60 minutes. During this time, they release nicotine at a relatively constant rate.

Monte (U.S. Pat. No. 5,810,018, 1998) described the use of a sequestering agent to facilitate the absorption of nicotine in the mouth when a nicotine containing solution is sprayed into the oral cavity. This procedure is inconvenient for the user and costly to manufacture.

Stanley and Haque were granted U.S. Pat. No. 5,824,334 on Oct. 20, 1998. They described a holder and a nicotine-containing tablet. Stanley's system requires the user to place the holder in his mouth like a cigarette holder whereupon the saliva dissolves the nicotine-containing tablet. Their procedure is more complicated than has been found necessary or desired. They obtain their short pulses of nicotine by physically removing the tablets from the subject's mouth. Their earlier U.S. Pat. No. 4,571,953, 1987 for a nicotine-containing lollipop is again for a removable nicotine source. It is similar to Mascarelli's device, supra.

OBJECTS AND ADVANTAGES

Accordingly one object of the present invention is to provide an improved way of delivering nicotine. Another object is to provide a means of supplying nicotine that satisfies the needs of cigarette smokers wishing to quit smoking. Still other objects are to provide a means of supplying nicotine to smokers under conditions where they are unable to smoke, to provide an inexpensive way of supplying nicotine, to supply nicotine in a way that is convenient for the user, and to supply nicotine in way that permits the user to vary the dosage to meet short-term needs.

Further objects and advantages will become apparent from a consideration of the ensuing description.

REFERENCE NUMERALS IN DRAWINGS

Figure 1:
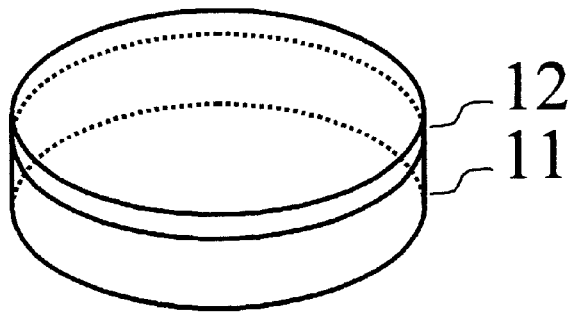
FIG. 1 is a perspective view of a tablet according to one embodiment of the present invention.

11 Non-nicotine containing matrix
12 Nicotine containing layer
13 Non-nicotine containing matrix
14 Nicotine containing layer
15 Non-nicotine containing layer
16 Nicotine containing layer
17 Non-nicotine containing matrix
18 Nicotine containing layer

SUMMARY

In accordance with the present invention a tablet comprises one or more rapidly dissolving layers, which contain nicotine or a nicotine-containing compound.

DESCRIPTION OF INVENTION

The novel invention is based on the finding that a short pulse of nicotine can be obtained in a transmucosal tablet by nicotine present in a thin layer on a core that does not contain nicotine. Appropriate thin layers containing nicotine can be prepared in many ways, as indicated by the following examples:

EXAMPLE 1

FIG. 1

A syrup was prepared by mixing 0.2004 gram of sucrose, 0.2017 gram of nicotine, and 0.2034 gram of water. As shown in FIG. 1, a thin layer 12 of this syrup was spread on top of an antacid matrix 11 with a paintbrush. The wet layer weighed 5.5 mg. The tablet was 1.7 cm in diameter and 0.4 cm thick. The total weight of the tablet was 1.5767 grams. The syrup was allowed to dry. In this example, the nicotine containing layer was about 0.002 cm thick. When the tablet was placed in the mouth, the layer containing nicotine dissolved in a few seconds and gave a short, intense pulse of about 1.8 mg of nicotine. Thereafter the non-nicotine matrix was allowed to dissolve in the mouth and swallowed along with the non-nicotine part of the nicotine layer.

It has been found that transmucosal administration of nicotine is not as efficient as smoking where the nicotine is absorbed in the lungs. This is similar to the findings of Stitzer and DeWitt, who used intravenous injections. Accordingly in the present invention larger amounts of nicotine were used than in most previously described studies.

EXAMPLE 2

FIG. 1

A mixture was made from 4.0289 grams of powdered calcium carbonate, 1.0683 grams of powdered magnesium hydroxide, 1.0856 grams of caffeine, and 40.4747 gram of powdered sucrose. One gram of the above powder mixture was placed in the cavity of a known tablet compression mold (not shown). The material was compressed to form a compact matrix, as shown at 11 in FIG. 1.

A second mixture was made of 0.6124 gram of nicotine tartrate and 8.0234 grams of sucrose.

The tablet-making device was opened and 0.0823 gram of the second mixture was sprinkled on top of the previously manufactured matrix. The plunger of the tablet-making device was reinserted and pressure applied to fuse the second mixture onto the previously manufactured matrix. The resulting compound two layered tablet was removed. Nicotine containing layer 12 is above and adherent to non-nicotine-containing matrix 11. When this tablet was placed in the mouth, nicotine layer 12 dissolved to provide a short pulse of about 1-mg of the nicotine base. Thereafter the non-nicotine base was allowed to dissolve in the mouth and swallowed along with the non-nicotine part of the nicotine layer.

The calcium carbonate and magnesium hydroxide have a basic reaction that promotes the absorption of the nicotine from nicotine tartrate. The addition of magnesium hydroxide to the calcium reduces the tendency of the calcium to cause constipation.

EXAMPLE 3

FIG. 2

Figure 2:
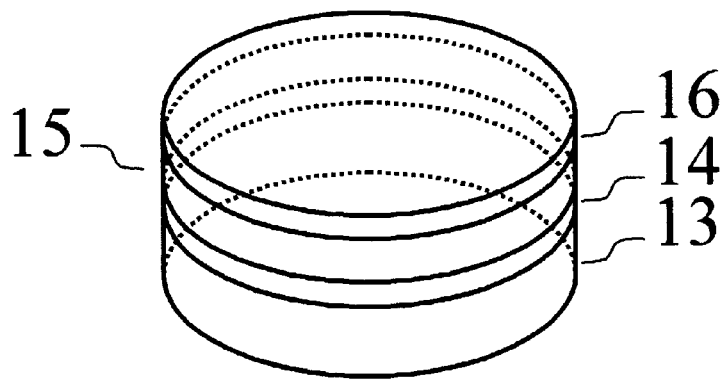
FIG. 2 is a perspective view of another embodiment of the tablet according to the invention.

One gram of the first mixture in Example 2 was placed in the cavity of a device for making tablets. The material was then compressed to a compact non-nicotine-containing matrix 13 (FIG. 2). The mold opened and 0.0631 gram of the second mixture of Example 2 was sprinkled on the top of the previously made, non-nicotine-containing matrix 13. The plunger was reinserted in the mold and pressure was used to fuse the second mixture onto the previously made non-nicotine containing matrix 13, thereby forming an overlying layer 14 containing nicotine.

The plunger was removed and 0.1256 gram of the first mixture from Example 2 was sprinkled on the top of the composite matrix 13 and layer 14. The plunger was reinserted into cavity of the mold and pressure used to fuse the new material on top of the matrix, thereby forming an overlying layer 15, which did not contain nicotine.

The plunger was removed and 0.0687 gram of the second mixture from Example 2 was sprinkled on top of the matrix 13 and layers 14 and 15. The plunger was again reinserted into the cavity of the mold and pressure applied to form an overlying, nicotine-containing layer 16 and to fuse all of the layers together to form a four layered tablet. I.e., the resulting tablet has a first non-nicotine containing matrix 13, a nicotine containing layer 14, a non-nicotine containing layer 15, and a second nicotine containing layer 16.

When placed in the mouth, the layers dissolved sequentially to provide two sharp pulses of nicotine separated by about one and a half minutes. The non-nicotine containing matrix and non-nicotine layers dissolve and are eventually swallowed along with the non nicotine part of the nicotine layers.

EXAMPLE 4

FIG. 3

Figure 3:
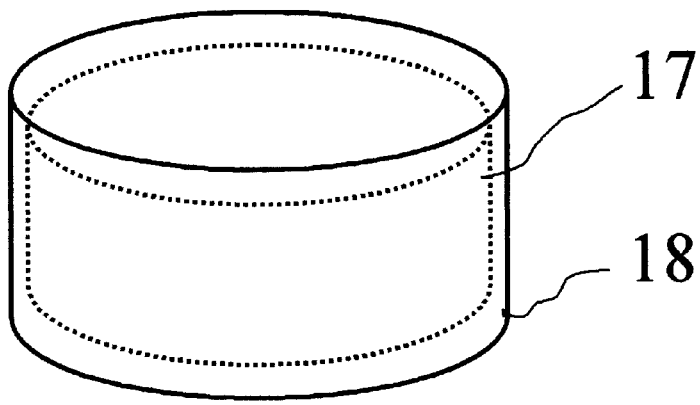
FIG. 3 is a perspective view of another embodiment of the tablet according to the invention.

Syrup was prepared by mixing 4.0412 grams of sucrose, 1.2018 grams of nicotine tartrate, and 10.6523 grams of water. An antacid tablet was dipped into the syrup and then allowed to dry. The dried tablet is shown in FIG. 3, where the original antacid is non-nicotine containing matrix 17 and is surrounded on all sides by the nicotine containing layer 18. The original weight of the antacid core was 1.5465 grams. The tablet, after dipping and drying weighed 1.5678 grams. When this tablet was placed in the mouth, the layer containing nicotine dissolved and gave a short, intense pulse of about 1.5 mg of nicotine.

OPERATION

A cigarette smoker can use any of the above examples to reduce or eliminate his need to smoke. The tablets of the above examples, when placed in the mouth give a short, intense pulse of nicotine that resemble the pharmacokinetics of cigarette smoking.

CONCLUSIONS, RAMIFICATIONS, AND SCOPE

From the above it is evident that tablets of the invention provide an improved way of delivering nicotine. Tablets of the invention can be made with any desired concentration of nicotine. Smokers can take tablets with decreasing concentration of nicotine and in time lose their addiction to nicotine. The availability of tablets with different concentrations of nicotine and by varying the times between tablets makes it possible for users to vary the dosage to meet short-term needs. The tablets can be made very inexpensively. They are convenient for the user to use. There are no social reasons that inhibit their use. These tablets do not have the adverse health considerations that smoking has. The tablets can be used to supply nicotine to smokers under conditions where they are unable to smoke.

While the above description contains many specificities, these should not be considered as limitations of the invention. For example, many alternative ways are available to make rapidly dissolving layers containing nicotine. The properties of rapidly dissolving layers containing nicotine or nicotine containing compounds will be determined by the geometry of the tablet, the thickness of the layers, and the materials employed. In the preferred embodiment, the layer that contains nicotine or nicotine containing compounds will dissolve in less than two minutes. The materials other than nicotine or nicotine containing compounds can include sugars, non-nutritive sweeteners, coloring agents, flavoring agents, binders and other compatible materials. In the preferred embodiment, the nicotine layer should contain the equivalent of from 0.5 mg to 5 mg of nicotine. In example 1, the nicotine-containing layer was about 0.002 cm thick. The sucrose and nicotine mixture dissolved in a few seconds. In example 2 the tablets were about 1.6 cm in diameter. The nicotine containing layer was about 0.004 cm thick. The thickness of the layer and the nature of the nicotine tartrate gave a layer that required 40 seconds to dissolve.

The part of the tablet not containing nicotine can be anything that is acceptable to take by mouth. It can contain caffeine, vitamins, flavoring materials, buffering agents, sugars, non-nutritive sweeteners, and other compatible materials.

Accordingly, the scope of the invention includes all those variations that fall within the scope of the appended claims and their legal equivalents.

I claim:

1. A nicotine containing tablet for transmucosal administration to an individual, said tablet comprising:

a) a non-toxic substrate matrix layer that does not contain nicotine comprising an antacid, b) a thin, nicotine containing layer comprising a pharmacological dose of nicotine of 0.5 mg to 5 mg wherein said nicotine containing layer is coated on or fused to said non-toxic substrate matrix layer, wherein said nicotine containing layer of said tablet when exposed to the human mouth dissolves in less than 2 minutes.

2. The tablet of claim 1 wherein said nicotine containing layer contains nicotine in its base form.

3. The tablet of claim 1 wherein said nicotine containing layer contains nicotine in the form of a nicotine salt compound.

4. The tablet of claim 1 wherein said matrix layer includes at least one agent that increases the pH of the oral cavity.

5. The tablet of claim 1 wherein said nicotine containing layer coats said matrix layer.

6. The tablet of claim 1 wherein said matrix layer further contains caffeine.

7. A method of treating nicotine dependency with the tablet of claim 1 comprising:

placing said tablet in the mouth of a nicotine-dependent individual, wherein the nicotine containing layer of said tablet dissolves and delivers a sharp pulse of nicotine to the body of the individual similar to that of smoking a cigarette.

8. A multi-layered nicotine containing tablet for use in transmucosal administration of nicotine to an individual, said multi-layered tablet comprising;

a) a non-toxic matrix layer that does not contain nicotine comprising an antacid, b) a thin, nicotine containing layer comprising a pharmacological dose of nicotine of between 0.5 mg and 5 mg, wherein said multi-layered tablet comprises alternating layers of a and b, said multi-layered tablet containing at least two layers of a and two layers of b and wherein each said nicotine containing layer of said multi-layered tablet sequentially dissolves in the human mouth in less than 2 minutes.

9. The tablet of claim 8 wherein said nicotine containing layer contains nicotine in its base form.

10. The tablet of claim 8 wherein said nicotine containing layer contains nicotine in the form of a nicotine salt compound.

11. The tablet of claim 8 wherein said matrix layer includes at least one agent that increases the pH of the oral cavity.

12. The tablet of claim 8 wherein said matrix layer further contains caffeine.

13. A method of treating nicotine dependency with the multi-layered tablet of claim 8 comprising:

placing said multi-layered tablet in the mouth of a nicotine-dependent individual wherein each said nicotine containing layer of said multi-layered tablet sequentially dissolves and delivers a sharp pulse of nicotine to the body of said individual similar to that of smoking a cigarette.

14. A nicotine containing multi-layered tablet for transmucosal administration to an individual, consisting of:

at least one alternating first and second layers, wherein each of said first layers does not contain nicotine and comprises a non-toxic matrix which is compatible with nicotine and dissolves in the mouth, and wherein each of said second layers is thin and comprises a pharmacological dose of nicotine of 0.5 mg to 5 mg, each of said thin, nicotine containing second layers is coated on or fused to each of said first layers, and each of said thin, nicotine containing second layers of said multi-layered tablet sequentially dissolves in the human mouth in less than 2 minutes.

15. A method of treating nicotine dependency with the multi-layered tablet of claim 14 comprising:

placing said multi-layered tablet in the mouth of a nicotine-dependent individual wherein each said nicotine containing layer of said multi-layered tablet sequentially dissolves and delivers a sharp pulse of nicotine to the body of said individual similar to that of smoking a cigarette.

\* \* \* \* \*